(12) United States Patent
Lee

(10) Patent No.: US 9,492,469 B2
(45) Date of Patent: Nov. 15, 2016

(54) COMBINATION THERAPY FOR THE TREATMENT OF PROLIFERATIVE DISEASES

(71) Applicant: Bristol-Myers Squibb Company, Princeton, NJ (US)

(72) Inventor: Francis Y. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/782,235

(22) PCT Filed: Apr. 4, 2014

(86) PCT No.: PCT/US2014/032899
§ 371 (c)(1),
(2) Date: Oct. 2, 2015

(87) PCT Pub. No.: WO2014/165718
PCT Pub. Date: Oct. 9, 2014

(65) Prior Publication Data
US 2016/0022723 A1 Jan. 28, 2016

Related U.S. Application Data

(60) Provisional application No. 61/808,378, filed on Apr. 4, 2013.

(51) Int. Cl.
| | | |
|---|---|---|
| *A01N 43/04* | (2006.01) | |
| *A61K 31/70* | (2006.01) | |
| *A61K 31/7068* | (2006.01) | |
| *A61K 31/5513* | (2006.01) | |
| *A61K 31/7064* | (2006.01) | |
| *A61K 31/706* | (2006.01) | |

(52) U.S. Cl.
CPC ....... *A61K 31/7068* (2013.01); *A61K 31/5513* (2013.01); *A61K 31/706* (2013.01); *A61K 31/7064* (2013.01)

(58) Field of Classification Search
None
See application file for complete search history.

(56) References Cited

U.S. PATENT DOCUMENTS

| | | | |
|---|---|---|---|
| 4,981,847 A | 1/1991 | Sato et al. | |
| 5,322,842 A | 6/1994 | Sato et al. | |
| 5,324,726 A | 6/1994 | Bock et al. | |
| 5,852,010 A | 12/1998 | Graham et al. | |
| 5,998,407 A | 12/1999 | Graham et al. | |
| 6,331,408 B1 | 12/2001 | Zaczek et al. | |
| 6,495,540 B2 | 12/2002 | Thompson | |
| 6,503,901 B1 | 1/2003 | Thompson et al. | |
| 6,503,902 B2 | 1/2003 | Olson et al. | |
| 6,509,333 B2 | 1/2003 | Olson | |
| 6,525,044 B2 | 2/2003 | Olson et al. | |
| 6,544,978 B2 | 4/2003 | Wu et al. | |
| 6,632,812 B2 | 10/2003 | Han et al. | |
| 6,653,303 B1 | 11/2003 | Wu et al. | |
| 6,713,476 B2 | 3/2004 | Yang et al. | |
| 6,737,038 B1 | 5/2004 | Zaczek et al. | |
| 6,756,511 B2 | 6/2004 | Castro Pineiro et al. | |
| 6,759,404 B2 | 7/2004 | Olson et al. | |
| 6,794,381 B1 | 9/2004 | Olson et al. | |
| 6,878,363 B2 | 4/2005 | Zaczek et al. | |
| 6,900,199 B2 | 5/2005 | Han et al. | |
| 6,958,329 B2 | 10/2005 | Olson | |
| 6,960,576 B2 | 11/2005 | Olson et al. | |
| 6,962,913 B2 | 11/2005 | Olson et al. | |
| 6,984,626 B2 | 1/2006 | Nadin et al. | |
| 7,001,901 B2 | 2/2006 | Yang | |
| 7,053,081 B2 | 5/2006 | Olson et al. | |
| 7,053,084 B1 | 5/2006 | Olson | |
| 7,101,870 B2 | 9/2006 | Olson et al. | |
| 7,105,509 B2 | 9/2006 | Castro Pineiro et al. | |
| 7,112,583 B2 | 9/2006 | Olson et al. | |
| 7,125,866 B1 | 10/2006 | Glick et al. | |
| 7,153,491 B2 | 12/2006 | Zaczek et al. | |
| 7,160,875 B2 | 1/2007 | Flohr et al. | |
| 7,276,495 B2 | 10/2007 | Han et al. | |
| 7,276,496 B2 | 10/2007 | Olson et al. | |
| 7,304,049 B2 | 12/2007 | Olson | |
| 7,304,055 B2 | 12/2007 | Olson et al. | |
| 7,304,056 B2 | 12/2007 | Olson et al. | |
| 7,342,008 B2 | 3/2008 | Olson et al. | |
| 7,354,914 B2 | 4/2008 | Olson | |

(Continued)

FOREIGN PATENT DOCUMENTS

| | | |
|---|---|---|
| EP | 0669334 | 8/1995 |
| WO | WO 97/36879 | 10/1997 |

(Continued)

OTHER PUBLICATIONS

Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.

Seiffert, D., et al., "Presenilin-1 and -2 Are Molecular Targets for gamma-Secretase Inhibitors," The Journal of Biological Chemistry, vol. 275, No. 44, pp. 34086-34091 (2000).

Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).

Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

Meredith, Jere, "Characterization of APP Activity and Notch Toxicity with gamma-Secretase Inhibitors," 8th International AD/PD Meeting, Salzberg, Austria, Mar. 17, 2007.

(Continued)

*Primary Examiner* — Patrick Lewis
(74) *Attorney, Agent, or Firm* — Gary D. Greenblatt

(57) ABSTRACT

A method of treating a proliferative disease, such as cancer, is disclosed. The method comprises administering to a mammal in need thereof synergistically therapeutically effective amounts of: (i) (2R,3S)—N-((3S)-1-methyl-2-oxo-5-phenyl-2,3-di-hydro-1H-1,4-benzodiazepin-3-yl)-2,3-bis (3,3,3-trifluoropropyl)succinamide; (ii) 2-deoxy-2,2-difluorocytidine monohydrochloride (beta-isomer); and (iii) optionally, one or more additional anticancer agents.

11 Claims, 2 Drawing Sheets

(56) References Cited

U.S. PATENT DOCUMENTS

| | | |
|---|---|---|
| 7,375,099 B2 | 5/2008 | Galley et al. |
| 7,390,802 B2 | 6/2008 | Han et al. |
| 7,390,896 B2 | 6/2008 | Olson et al. |
| 7,423,033 B2 | 9/2008 | Olson et al. |
| 7,456,172 B2 | 11/2008 | Olson |
| 7,456,278 B2 | 11/2008 | Olson |
| 7,498,324 B2 | 3/2009 | Han et al. |
| 7,528,249 B2 | 5/2009 | Olson et al. |
| 7,544,679 B2 | 6/2009 | Flohr et al. |
| 7,582,624 B2 | 9/2009 | Carter et al. |
| 7,655,647 B2 | 2/2010 | Han et al. |
| 7,718,795 B2 | 5/2010 | Olson |
| 8,629,136 B2 | 1/2014 | Gavai et al. |
| 8,822,454 B2 | 9/2014 | Gavai et al. |
| 8,999,918 B2 | 4/2015 | Gavai et al. |
| 2007/0185094 A1 | 8/2007 | Lattmann et al. |
| 2009/0181944 A1 | 7/2009 | Boylan et al. |
| 2012/0245151 A1* | 9/2012 | Gavai ............... A61K 31/5513 514/221 |
| 2014/0357605 A1 | 12/2014 | Gavai et al. |

FOREIGN PATENT DOCUMENTS

| | | |
|---|---|---|
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047369 | 3/2014 |
| WO | WO 2014/047370 | 3/2014 |
| WO | WO 2014/047374 | 3/2014 |
| WO | WO 2014/047390 | 3/2014 |
| WO | WO 2014/047391 | 3/2014 |
| WO | WO 2014/047392 | 3/2014 |
| WO | WO 2014/047393 | 3/2014 |
| WO | WO 2014/047397 | 3/2014 |

OTHER PUBLICATIONS

Prasad, C.V.C., et al., "Discovery of (S)-2-((S)-2(3,5-difluorophenyl)-2-hydroxyacetam ido)-N-((S,Z)-3-methyl-4-oxo-4,5-dihydro-3H-benzo[d][1,2]diazepin-5-yl)propanamide (BMS-433796): A gamma-secretase inhibitor with a beta lowering activity in a transgenic mouse model of Alzheimer's disease," Bioorganic & Medicinal Chemistry Letters 17 pp. 4006-4011 (2007).

Jun, H.T., et al., "Top NOTCH Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

Egloff, A.M., et al., "Molecular Pathways: Context-Dependent Approaches to Notch Targeting as Cancer Therapy," Clinical Cancer Research, vol. 18, No. 19, pp. 5188-5195 (Jul. 6, 2012).

Yabuuchi, S., et al., "Notch signaling pathway targeted therapy suppresses tumor progression and metastatic spread in pancreatic cancer," Cancer Letters, vol. 335, pp. 41-51 (Feb. 9, 2013).

Zardavas, D., et al., "Personalized therapy for breast cancer: A dream or a reality?", Future Oncology. Future Medicine Ltd., London, GB, vol. 9, No. 8, pp. 1105-1119 (Aug. 1, 2013).

PCT/US2014/032899 International Search Report mailed Jul. 9, 2014.

PCT/US2014032899 Preliminary Report on Patentability mailed Oct. 15, 2015.

* cited by examiner

COMBINATION THERAPY FOR THE TREATMENT OF PROLIFERATIVE DISEASES

CROSS REFERENCE TO RELATED APPLICATIONS

This application is a national phase application under 35 U.S.C. §371 of International Patent Application No. PCT/US2014/032899, filed Apr. 4, 2014, which claims priority to U.S. Provisional Application 61/808,378, filed Apr. 4, 2013, which are expressly incorporated fully herein by reference.

DESCRIPTION

This invention relates to the fields of oncology and improved chemotherapy regimens.

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed. Anticancer agents have been classified based upon their mechanism of action.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell* 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Preseniln 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anticancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

U.S. Patent Publication No. 2012/245151A discloses the Notch inhibitor compound of Formula (I):

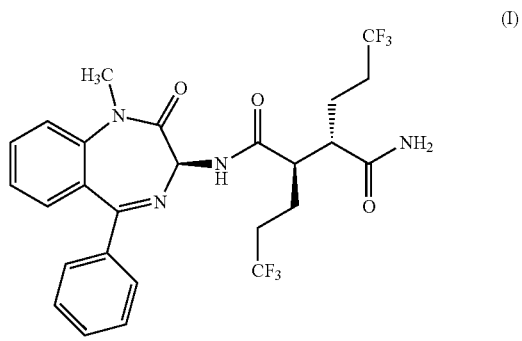 [SMILES: CN1C(=O)[C@@H](NC(=O)[C@H](CCC(F)(F)F)[C@H](CCC(F)(F)F)C(N)=O)N=C(c2ccccc2)c2ccccc21]

which has the chemical name (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide. The reference, which discloses a synthesis process for preparing the compound, is incorporated by reference herein in its entirety.

The present invention is directed to a method of treating a proliferative disease such as cancer, which comprises administering a synergistic, therapeutically effective amount of (i) the Notch inhibitor compound of Formula (I); (ii) gemcitabine or a pharmaceutically acceptable salt thereof; and (iii) optionally, one or more additional anticancer agents.

SUMMARY OF THE INVENTION

The present invention also provides a method for the treatment of cancer, which comprises administering to a mammal in need thereof a synergistically therapeutically effective amount of: (i) (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide; (ii) 2'-deoxy-2',2'-difluorocytidine monohydrochloride (beta-isomer); and (iii) optionally, one or more additional anticancer agents.

BRIEF DESCRIPTIONS OF THE DRAWINGS

The invention is illustrated by reference to the accompanying drawings described below. "Cmpd(I)" and "Compound (I)" refer to the Compound of Formula (I). "Gem" refers to gemcitabine hydrochloride.

DETAILED DESCRIPTION

Figure 1:
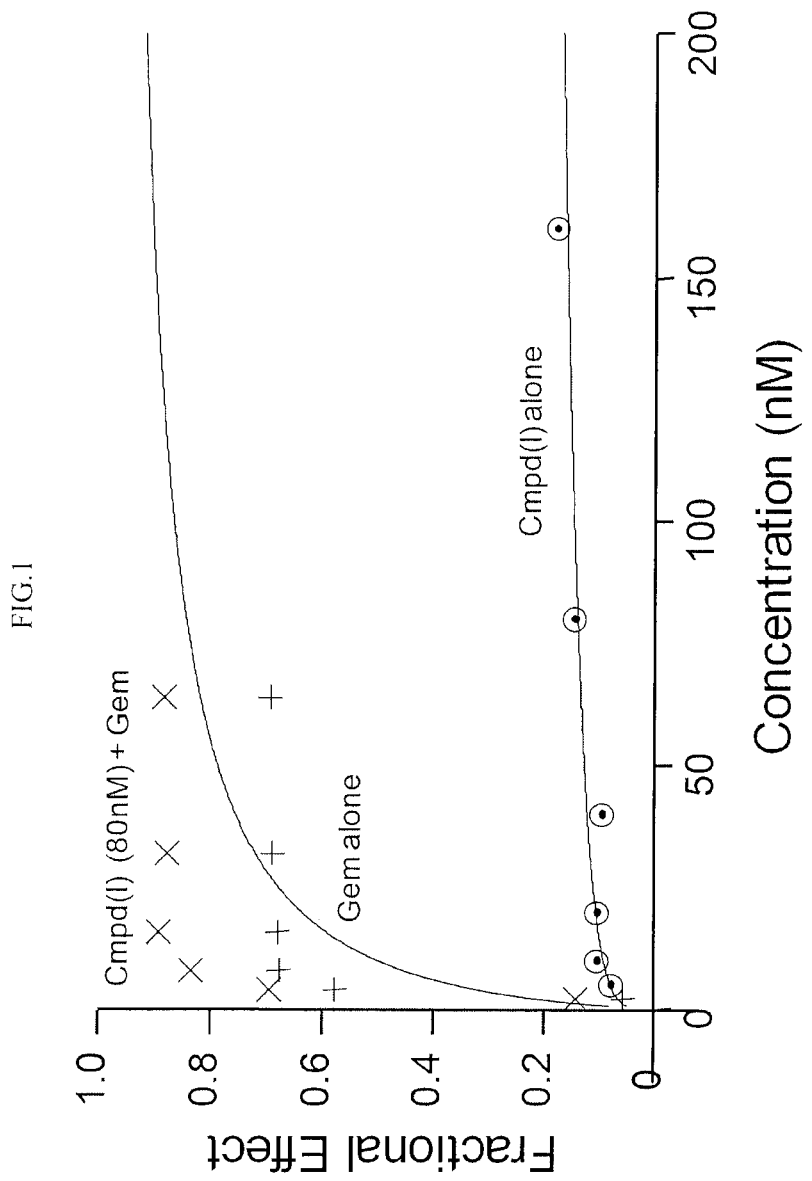
FIG. 1 shows the activity of Compound (I) alone and in combination with gemcitabine on SK-LU-1 human non-small cell carcinoma cells in vitro. Concentration effect of each agent alone and in combination was assessed by MTT assay after 72 hours of culture.
Figure 2:
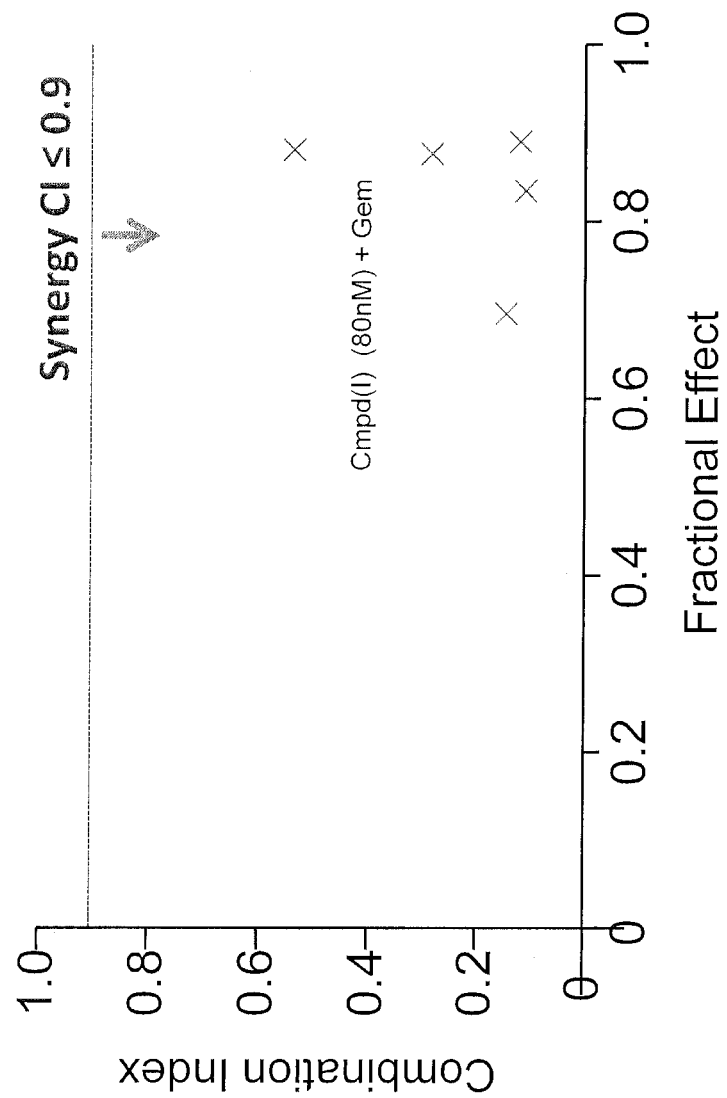
FIG. 2 shows the algebraic estimate of the cell kill versus combination index (CI) plot of Compound (I) at 80 nM concentration combined with various concentrations of gemcitabine. CI values were less than 0.9 at multiple combination ratios indicating that the combined effects of the two agents were highly synergistic.

The first aspect of the present invention provides a method for the treatment of cancer, which comprises administering to a mammal in need thereof a synergistically therapeutically effective amount of: (i) (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide; (ii) 2'-deoxy-2',2'-difluorocytidine monohydrochloride (beta-isomer); and (iii) optionally, one or more additional anticancer agents.

The anticancer drug, 2'-deoxy-2',2'-difluorocytidine monohydrochloride (beta-isomer), is the monohydrochloric acid salt of the compound having the structure of Formula (II):

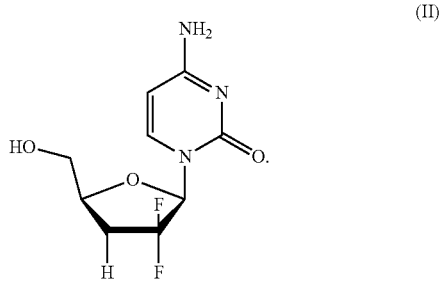

The drug is known in the art as gemcitabine hydrochloride and is sold as GEMZAR® (Eli Lilly and Company).

In one embodiment, a method is provided for the treatment of cancer, which comprises administering to a mammal in need thereof a synergistically therapeutically effective amount of: (i) (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide; and (ii) 2'-deoxy-2',2'-difluorocytidine monohydrochloride (beta-isomer).

In one embodiment, a method is provided for the treatment of cancer, which comprises administering to a mammal in need thereof a synergistically therapeutically effective amount of (i) (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide; and (ii) 2'-deoxy-2',2'-difluorocytidine monohydrochloride (beta-isomer); wherein 2R,3S)—N-((3S)-1-methyl-2-oxo-5-phenyl-2,3-dihydro-1H-1,4-benzodiazepin-3-yl)-2,3-bis(3,3,3-trifluoropropyl)succinamide is administered prior to administration of 2'-deoxy-2',2'-difluorocytidine monohydrochloride (beta-isomer).

In one embodiment, a method is provided for the treatment of cancer, which comprises administering to a mammal in need thereof a synergistically therapeutically effective amount of (i) (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide; and (ii) 2'-deoxy-2',2'-difluorocytidine monohydrochloride (beta-isomer); wherein 2R,3S)—N-((3S)-1-methyl-2-oxo-5-phenyl-2,3-dihydro-1H-1,4-benzodiazepin-3-yl)-2,3-bis(3,3,3-trifluoropropyl)succinamide is simultaneously with 2'-deoxy-2',2'-difluorocytidine monohydrochloride (beta-isomer).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compound in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising the compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

UTILITY

The compound of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

The method of this invention can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this invention is used to treat breast cancer, colon cancer, or pancreatic cancer. Preferably, the mammal is a human.

In one embodiment, the method of this invention is used to treat triple negative breast cancer. Preferably, the mammal is a human.

In one embodiment, the method of this invention is used to treat cancer, wherein said cancer has a translocation of at least one of the Notch receptors. For example, human triple negative breast carcinoma HCC-1599 has a Notch 1 translocation.

In one embodiment, the method of this invention is used to treat cancer, wherein said cancer, wherein said cancer is non-small cell lung cancer. Preferably, the mammal is a human.

In one embodiment, the method of this invention is used to treat cancer, wherein said cancer, wherein said cancer is pancreatic cancer. Preferably, the mammal is a human.

In one embodiment, the method of this invention is used to treat cancer, wherein said cancer, wherein said cancer is ovarian cancer. Preferably, the mammal is a human.

In one embodiment, the method of this invention is used to treat cancer, wherein said cancer, wherein said cancer is melanoma. Preferably, the mammal is a human.

In one embodiment, the method of this invention is used to treat cancer, wherein the cancer is dependent upon Notch activation. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In treating cancer, a combination of chemotherapeutic agents and/or other treatments (e.g., radiation therapy) is often advantageous. In the method of this invention, in addition to the compound of Formula (I) and 2'-deoxy-2',2'-difluorocytidine monohydrochloride (beta-isomer), one or more additional anticancer agents may be optionally administered. This optional third agent may have the same or different mechanism of action than the two primary therapeutic agents. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The invention herein further comprises use of the compound of Formula (I) in preparing medicaments for the treatment of cancer, and/or it comprises the packaging of a compound of Formula (I) herein together with instructions that the compound be used in combination with 2'-deoxy-2',2'-difluorocytidine monohydrochloride (beta-isomer) for the treatment of cancer. The present invention further comprises combinations of the compound of Formula (I); and 2'-deoxy-2',2'-difluorocytidine monohydrochloride (beta-isomer) in kit form, e.g., where they are packaged together or placed in separate packages to be sold together as a kit, or where they are packaged to be formulated together.

In the method of this invention, either of both of the compound of Formula (I) and 2'-deoxy-2',2'-difluorocytidine monohydrochloride (beta-isomer) can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

A therapeutically effective of Compound (I) includes doses in the range of greater than 2 mg to 8 mg including, for example, 3, 4, 5, 6, 7, and 8 mg. The therapeutically effective dose of Compound (I) can be administered as a single dose or as multiple doses. For example, 6 mg of Compound (I) can be administered as two separate 3 mg doses.

A therapeutically effective of gemcitabine includes doses in the range of greater than 500 $mg/m^2$ to 1500 $mg/m^2$ including, for example, 500, 600, 700, 800, 900, 1000, 1100, 1200, 1300, 1400, and 1500 $mg/m^2$. The therapeutically effective dose of gemcitabine can be administered as a single dose or as multiple doses. For example, 1000 $mg/m^2$ of Compound (I) can be administered as two separate 500 $mg/m^2$ doses.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the compound of Formula (I) is administered continuously to a patient in need thereof, one or more times daily. For example, a therapeutically effective amount of the compound of Formula (I) is administered to a patient in need thereof, one or more times daily for continuous days.

In one embodiment, the compound of Formula (I) is administered intermittently to a patient in need thereof, one or more times daily. For example, a therapeutically effective amount of the compound of Formula (I) is administered to a patient in need thereof, one or more times daily according to an intermittent schedule.

In one embodiment, the compound of Formula (I) is administered to a patient in need thereof, one or more times daily for continuous days followed by one or more days without administration. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, the compound of Formula (I) is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, the compound of Formula (I) is administered on one day, followed by 6 days of rest, and repeated on a weekly schedule.

In one embodiment, the compound of Formula (I) is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, the compound of Formula (I) is administered on two consecutive days, followed by 5 days of rest, and repeated on a weekly schedule.

In one embodiment, the compound of Formula (I) is administered on three consecutive days followed by four days of rest, and repeated on a weekly schedule.

In one embodiment, the compound of Formula (I) is administered on one day, followed by 10 to 13 days of rest.

In one embodiment, the compound of Formula (I) is administered once each day (QD). This embodiment include once daily oral administration.

In one embodiment, the compound of Formula (I) is administered twice each day (BID). This embodiment include twice daily oral administration.

In one embodiment, the compound of Formula (I) is administered on alternate days: one day on followed by one day of rest. This two day cycle can be repeated one or more times.

In one embodiment, the combination of the compound of Formula (I) and gemcitabine are administered one day, followed by 6 days of rest, and repeated on a weekly schedule.

In one embodiment, Compound (I) is administered at a dose of from greater than 2 mg to 8 mg; and gemcitabine is administered at a dose of 500-1500 $mg/m^2$. For example, in this embodiment, Compound (I) and gemcitabine are administered once weekly, either on the same day or on different days of the week. Suitable doses of Compound (I) include 3, 4, 5, 6, 7, and 8 mg. Suitable doses of gemcitabine include 500, 600, 700, 800, 900, 1000, 1100, 1200, 1300, 1400, and 1500 $mg/m^2$.

In one embodiment, Compound (I) is administered at a dose of from 3 mg to 8 mg; and gemcitabine is administered at a dose of 500-1500 mg/m². Administration schedules include once weekly administration of Compound (I) and gemcitabine, either on the same day or on different days of the week.

BIOLOGICAL ASSAYS

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

In vitro cytotoxicity was assessed in tumor cells using a tetrazolium-based colorimetric assay that exploits the metabolic conversion of MTS (3-(4,5-dimethylthiazol-2-yl)-5-(3-carboxymethoxyphenyl)-2-(4-sulphenyl)-2H-tetrazolium, inner salt) to a reduced form detectable via measurement of light absorption at 492 nm. Cells were seeded at $4 \times 10^3$/well in 96-well plates 24 h prior to drug addition. Following 72 hours of dasatinib treatment, a combination of MTS and phenazine methosulfate was added to the wells, and cells were incubated for a further 3 hours. The number of surviving cells was measured relative to control populations.

Drug interaction analysis and the confirmation of synergism was determined by the method of Chou and Talalay. Linear regression analysis of dose-response data was performed using Calcusyn 1.2 software (Biosoft, Cambridge, United Kingdom) to calculate a combination index (CI) for each individual drug combination. To ensure valid statistical analysis, only experimental data for which the linear correlation coefficient of the median-effect plot was more than 0.9 were included. CI values were defined as:

| CI | Definition |
| --- | --- |
| CI ≤ 0.3 | strongly synergistic |
| 0.3 < CI ≤ 0.9 | synergistic |
| 0.9 < CI ≤ 1.1 | additive |
| 1.1 < CI ≤ 3.3 | antagonistic |
| 3.3 < CI | strongly antagonistic |

CI for Combination of Compound (I) and Gemcitabine

| Cmpd (I) (nM) | Gemcitabine (nM) | Fractional Effect | CI |
| --- | --- | --- | --- |
| 80 | 2 | 0.144 | 2.764 |
| 80 | 4 | 0.696 | 0.145 |
| 80 | 8 | 0.835 | 0.109 |
| 80 | 16 | 0.891 | 0.120 |
| 80 | 32 | 0.877 | 0.284 |
| 80 | 64 | 0.882 | 0.535 |

Combination of the compound of Formula (I) with gemcitabine hydrochloride in models of human non-small cell lung carcinoma in vitro led to synergistic cell kill. Specifically the compound of Formula (I) when used at concentrations between 10-80 nM (concentrations that are relevant in patients) in combination with gemcitabine at concentrations greater than 2 nM was shown to produce synergistic cell killing in the SK-LU-1 human non-small cell lung carcinoma cell line.

What is claimed is:

1. A method of treating cancer comprising administering sequentially or concurrently to a human in need thereof, a synergistically therapeutically effective amount of (i) (2R,3S)—N-((3S)-1-methyl-2-oxo-5-phenyl-2,3-dihydro-1H-1,4-benzodiazepin-3-yl)-2,3-bis(3,3,3-trifluoropropyl)succinamide; and (ii) 2'-deoxy-2',2'-difluorocytidine monohydrochloride (beta-isomer).

2. The method according to claim 1 wherein 2R,3S)—N-((3S)-1-methyl-2-oxo-5-phenyl-2,3-dihydro-1H-1,4-benzodiazepin-3-yl)-2,3-bis(3,3,3-trifluoropropyl)succinamide is administered prior to administration of 2'-deoxy-2',2'-difluorocytidine monohydrochloride (beta-isomer).

3. The method according to claim 1 wherein 2R,3S)—N-((3S)-1-methyl-2-oxo-5-phenyl-2,3-dihydro-1H-1,4-benzodiazepin-3-yl)-2,3-bis(3,3,3-trifluoropropyl)succinamide is administered simultaneously with 2'-deoxy-2',2'-difluorocytidine monohydrochloride (beta-isomer).

4. The method according to claim 1 wherein (2R,3S)—N-((3S)-1-methyl-2-oxo-5-phenyl-2,3-dihydro-1H-1,4-benzodiazepin-3-yl)-2,3-bis(3,3,3-trifluoropropyl) succinamide is administered at a dose of greater than 2 mg to 8 mg.

5. The method according to claim 1 wherein 2'-deoxy-2',2'-difluorocytidine monohydrochloride (beta-isomer) is administered at a dose of from 500 mg/m² to 1500 mg/m².

6. The method according to claim 1 wherein said cancer is non-small cell lung cancer, pancreatic cancer, or breast cancer.

7. The method according to claim 1 wherein said cancer is non-small cell lung cancer.

8. The method according to claim 1 wherein (2R,3S)—N-((3S)-1-methyl-2-oxo-5-phenyl-2,3-dihydro-1H-1,4-benzodiazepin-3-yl)-2,3-bis(3,3,3-trifluoropropyl) succinamide is administered at a dose of greater than 2 mg to 8 mg; and 2'-deoxy-2',2'-difluorocytidine monohydrochloride (beta-isomer) is administered at a dose of from 500 mg/m² to 1500 mg/m².

9. The method according to claim 8 wherein said cancer is non-small cell lung cancer.

10. The method according to claim 1 wherein (2R,3S)—N-((3S)-1-methyl-2-oxo-5-phenyl-2,3-dihydro-1H-1,4-benzodiazepin-3-yl)-2,3-bis(3,3,3-trifluoropropyl) succinamide is administered at a dose of greater than 2 mg to 8 mg once weekly.

11. The method according to claim 10 wherein said cancer is non-small cell lung cancer.

* * * * *

UNITED STATES PATENT AND TRADEMARK OFFICE
CERTIFICATE OF CORRECTION

PATENT NO.        : 9,492,469 B2
APPLICATION NO.   : 14/782235
DATED             : November 15, 2016
INVENTOR(S)       : Francis Y Lee It is certified that error appears in the above-identified patent and that said Letters Patent is hereby corrected as shown below:

In the Claims

Claim 2, Column 14, Line 25, delete "2R,3S)" and insert -- (2R,3S) --;

Claim 3, Column 14, Line 30, delete "2R,3S)" and insert -- (2R,3S) --;

Claim 4, Column 14, Line 37, delete "trifluoropropyl) succinamide" and insert -- trifluoropropyl)succinamide --;

Claim 8, Column 14, Line 48, "trifluoropropyl) succinamide" and insert -- trifluoropropyl)succinamide --; and Claim 10, Column 14, Line 57, delete "trifluoropropyl) succinamide" and insert -- trifluoropropyl)succinamide --.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*